United States Patent
Martineau

[19]

[11] Patent Number: 6,135,130
[45] Date of Patent: Oct. 24, 2000

[54] WASHER WITH A DOUBLE PANE WINDOW

[75] Inventor: Louis Martineau, St-Nicholas, Canada

[73] Assignee: Steris Corporation, Mentor, Ohio

[21] Appl. No.: 09/244,854

[22] Filed: Feb. 4, 1999

Related U.S. Application Data

[60] Provisional application No. 60/073,672, Feb. 4, 1998.

[51] Int. Cl.[7] ....................................................... A47L 15/42
[52] U.S. Cl. ........................... 134/113; 126/200; 134/201
[58] Field of Search ..................... 134/201, 113; 126/198, 200; 220/377

[56] References Cited

U.S. PATENT DOCUMENTS

| | | | |
|---|---|---|---|
| 2,450,670 | 10/1948 | Loeb | 220/377 X |
| 3,088,474 | 5/1963 | Leslie | 134/113 |
| 3,489,135 | 1/1970 | Astrella | 126/200 X |
| 3,577,973 | 5/1971 | Katona | 126/200 |
| 4,033,321 | 7/1977 | Krebs | 126/198 |
| 4,041,930 | 8/1977 | Katona | 126/198 |
| 4,043,091 | 8/1977 | Katona | 126/200 X |
| 4,817,585 | 4/1989 | Craver | 126/200 |

FOREIGN PATENT DOCUMENTS

| | | |
|---|---|---|
| 343151 A2 | 5/1989 | European Pat. Off. . |
| 821 113 | 11/1951 | Germany . |

*Primary Examiner*—Philip R. Coe
*Attorney, Agent, or Firm*—Fay, Sharpe, Fagan, Minnich & McKee, LLP

[57] ABSTRACT

A dismantlable door (22) seals an opening (24) in a chamber (20) of a washer. The door includes removable glass panes (36) and (38) which allow an operator to view the contents of the washing chamber during a washing cycle. A connecting member (40, 132, 156, 180, 200, 216, 220, 244, 250) seals the inner glass pane (36) to a frame (28) of the door by compressing a gasket (42). In one preferred embodiment, the connecting member also receives a lower end 102 of the outer pane (38) in a channel (100, 202'). In other preferred embodiments a channel (131, 242) or L-shaped flange (224) is connected with the lower end of the door frame for supporting the lower end (102) of the outer glass pane. In yet another preferred embodiment, fixing members (258) connect the outer glass pane to the connecting member. An air space (170) is formed between the inner and outer panes. Air is able to enter and leave the air space through air gaps between the channel and the outer panes. This allows the pressure within the air space to equilibrate and allows the two panes to flex independently in response to changes in surrounding ambient conditions. The outer pane can be removed from the channel or L-shaped flange for replacement or cleaning of the panes. The inner and outer panes can both be removed by unscrewing the connecting member from the door frame.

24 Claims, 10 Drawing Sheets

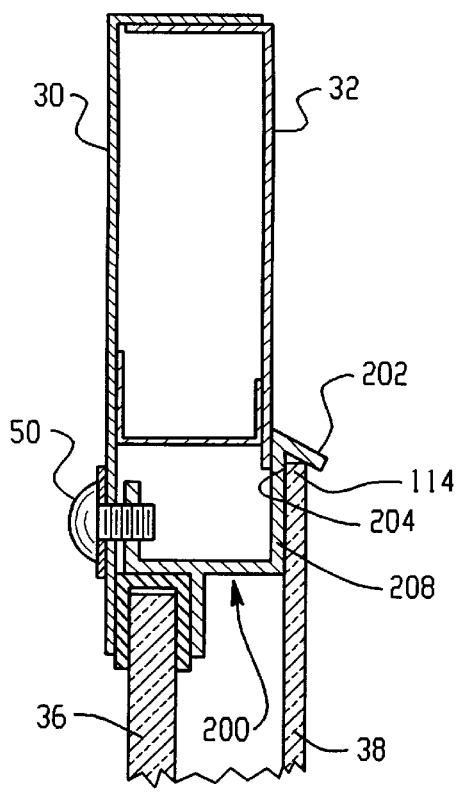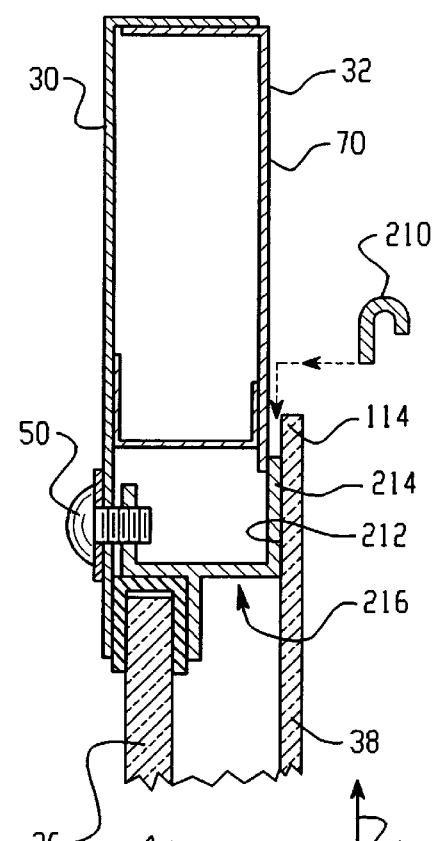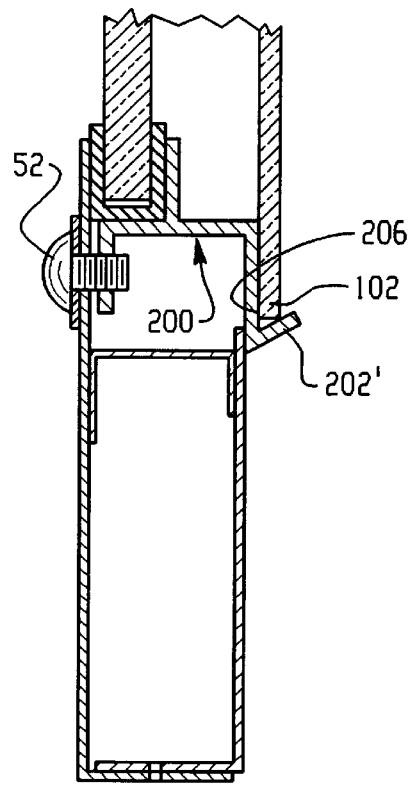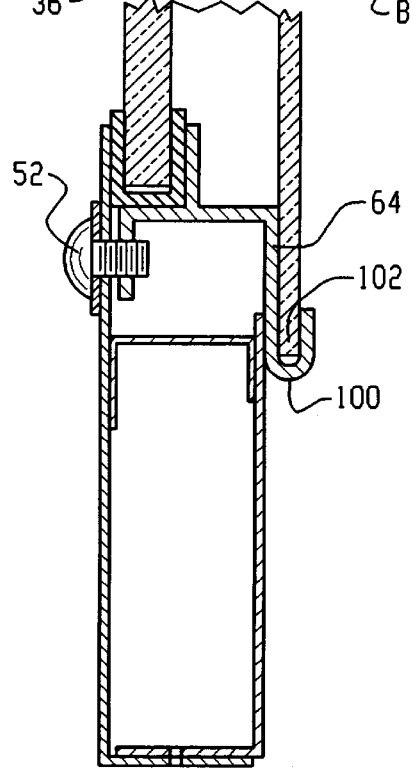
Fig. 10    Fig. 11

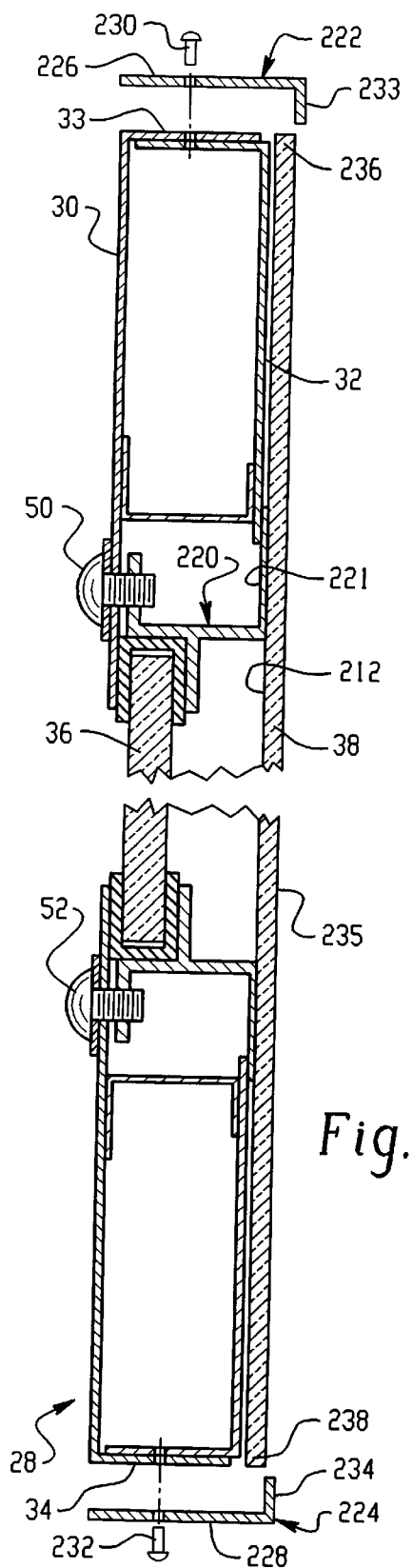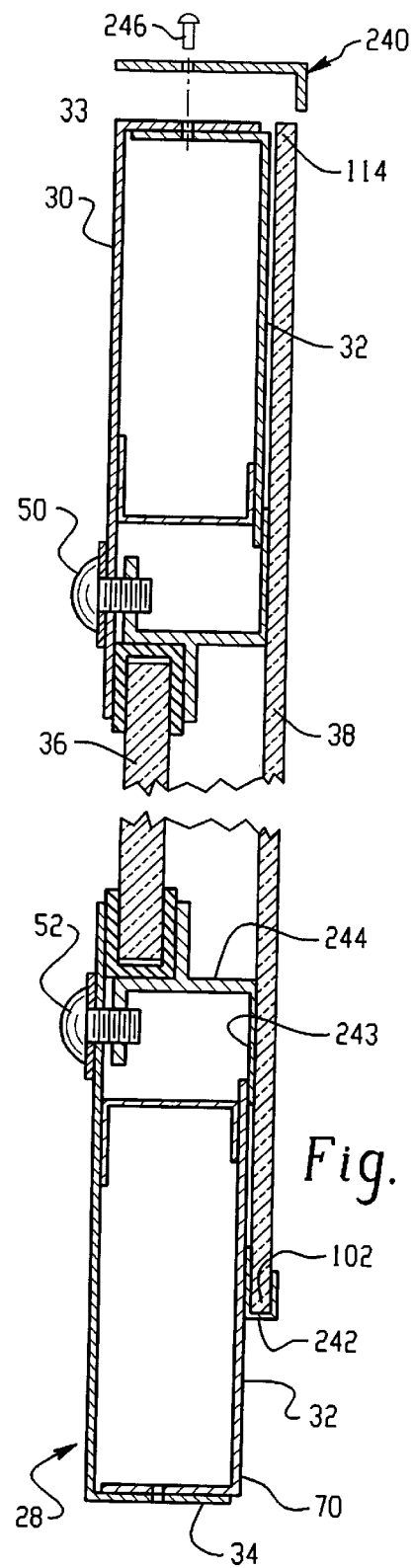

WASHER WITH A DOUBLE PANE WINDOW

This application claims priority from Provisional Application Serial No. 60/073,672, filed Feb. 4, 1998.

BACKGROUND OF THE INVENTION

The present invention relates to the decontamination arts. It finds particular application in conjunction with glass-paneled doors for washing or disinfecting equipment, and will be described with particular reference thereto. It should be appreciated, however, that the invention is also applicable to a wide variety of equipment that is operated at high humidities for which it is desirable for visibility of items enclosed within the equipment to be maintained.

Conventional, large-scale washers for sterilizing, cleaning or disinfecting larger pieces of medical equipment, animal cages and racks, and the like, often incorporate washer doors equipped with insulating glass units which allow the operators to see inside the washer chamber during operation. Such glass units are typically installed through an interior side of the door and clamped in position. The insulating units are used to minimize outside surface temperature of the glass to prevent accidental burns to the operator. British standard 4086:1966, for example, specifies a maximum allowable exterior temperature of 158° F. The glass units typically have a sealed air cavity or a vacuum space as an insulator. An insulating seal, between inner and outer panes of glass, seals the air cavity or vacuum space.

The high temperatures reached in the washing cycle mechanically stress the insulating seal, particularly the hotter inner pane relative to the cooler outer pane. The interior of the washer not only has higher temperatures and pressures, but also higher humidity. A fractured seal permits some of the humid air to enter and become trapped between the panes. When the humidity level in the cooler cavity becomes too high, condensation problems tend to occur. The condensation is typically removed by replacing the expensive double-paned window assembly.

The present invention provides for a new and improved dismantlable door with a double pane window which overcomes the above referenced problems and others.

SUMMARY OF THE INVENTION

In accordance with one aspect of the present invention, a washer is provided. The washer includes a washing chamber for receiving items to be washed at elevated temperatures using chemical detergents and a dismantlable door for permitting selective access for loading items into and unloading items from the washing chamber. The door comprises a support frame, an inner glass pane, an outer glass pane, and a connecting member. The connecting member is configured for selectively maintaining the inner glass pane and the frame in a sealing relation and for selectively receiving the outer glass pane in an unsealed relation to the frame.

In accordance with another aspect of the present invention, a connecting assembly for selectively maintaining an inner transparent pane in sealing relation with a washer door frame and for selectively receiving an outer transparent pane is provided. The connecting assembly includes a first peripheral flange which is configured for attachment to an inner door frame panel, a second peripheral flange for selectively engaging an outer face of an outer door frame panel, the second peripheral flange defining a channel along at least a lower edge for receiving at least a lower edge of the outer transparent pane, and a third peripheral flange for engaging an outer peripheral edge of the inner transparent pane to hold the inner transparent pane between the third flange and an outer face of the inner door panel. The second and third flanges are configured for positioning the inner and outer transparent panes in a spaced relationship such that an airspace is defined therebetween.

One advantage of the present invention is that it eliminates the condensation between the panes of glass within the door of a washer while retaining a maximum outside glass surface temperature within the specified range.

Another advantage of the present invention is that it limits the expansion of the panes of glass.

Yet another advantage of the present invention is that it enables removal of the glass unit for easy cleaning or partial replacement of the glass panes of the door.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

FIG. 10 is a side sectional view of the dismantlable door of FIG. 1 in accordance with a fifth embodiment of the present invention;

FIG. 11 is a side sectional view of the dismantlable door of FIG. 1 in accordance with a sixth embodiment of the present invention;

FIG. 12 is a partially exploded side sectional view of the dismantlable door of FIG. 1 in accordance with a seventh embodiment of the present invention;

FIG. 13 is a side sectional view of the dismantlable door of FIG. 1 in accordance with an eighth embodiment of the present invention;

DETAILED DESCRIPTION OF THE PREFERRED EMBODIMENTS

Figure 1:
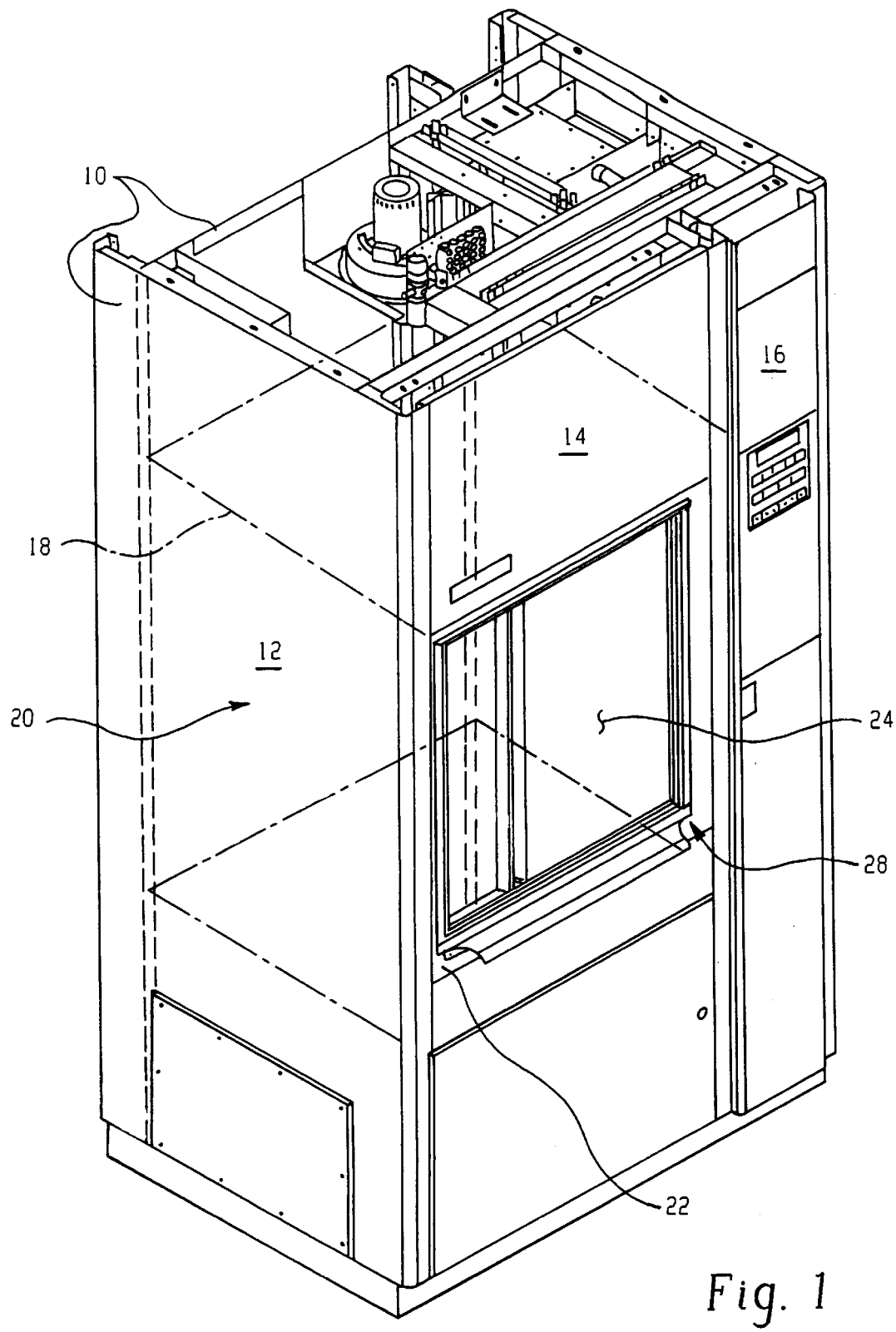
FIG. 1 is a perspective view of a washer with a dismantlable door according to the present invention.

With reference to FIG. 1, a washer suitable for cleaning, sterilizing, and disinfecting laboratory and medical equipment, animal cages and racks, and the like, includes a frame 10 which supports side panels 12, and front panels 14 and 16. Mounted to the frame is a vessel 18 which defines a washing chamber 20. A dismantlable door 22 seals an opening 24 in the vessel 18. The door is preferably defined in a portion of the front panel 14. Items to be cleaned, sterilized or disinfected are loaded into the chamber 20 through the door. The door is then closed to seal the vessel opening during a washing cycle.

With reference also to FIGS. 2–5, the door includes a rectangular door frame 28. The door frame includes an inner panel 30, which faces the interior of the chamber 20, and an outer panel 32, which faces the exterior of the washer. The inner and outer panels are sealed together adjacent their extremities 33 and 34 to define an inner cavity 35. Optionally, an insulating material is packed into the inner cavity 35.

The panels 30, 32 of the frame are preferably manufactured from stainless steel or other suitable materials which are coated with a coating which is resistant to the chemicals and environmental conditions used in the washing vessel.

The door also includes removable inner and outer transparent panes 36 and 38, respectively, which are releasably mounted to the door frame 28 by a connecting member or bracket 40. The panes allow an operator to view the contents of the chamber during a washing cycle. While the washer is described with reference to a dismantlable door, it should be appreciated that the removable panes need not be fitted into the door of the washer. Alternatively, the panes and connecting member are mounted such that they allow viewing of the chamber contents through a side wall or other portion of the chamber.

The panes 36 and 38 are preferably formed from a tempered glass which is resistant to the chemicals used in the washer. Preferably, the inner glass pane 36 has sufficient thickness and strength to withstand the physical and chemical conditions within the washer chamber. A tempered glass of about 6 millimeters in thickness is preferred. The outer glass pane 38 does not have to withstand the same temperature fluctuations and chemical conditions as the inner pane, and may therefore be thinner. A tempered glass of about 3 millimeters in thickness is sufficient for the outer pane 38.

Figure 3:
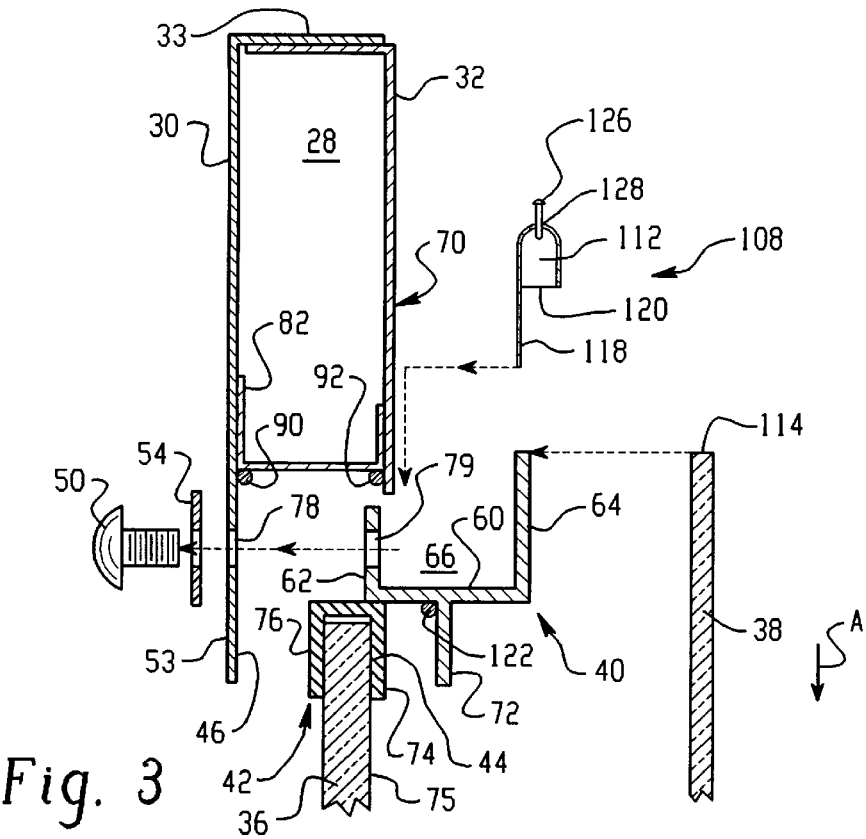
FIG. 3 is an exploded side sectional view of an upper section of the dismantlable door of FIG. 1 in accordance with a first embodiment of the present invention.
Figure 4:
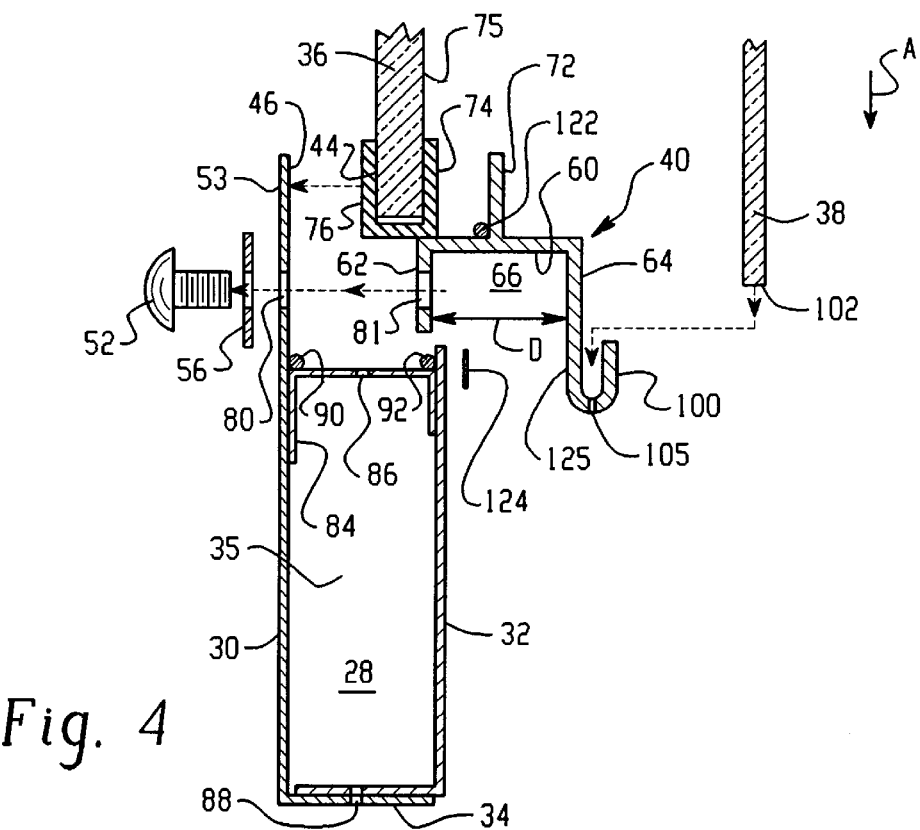
FIG. 4 is an exploded side view of a lower section of the dismantlable door of FIG. 1 in accordance with the embodiment of FIG. 3.

A sealing member, such as a rectangular gasket 42 with a U-shaped cross section, receives a peripheral edge 44 of the inner pane. The U-shaped gasket 42 is preferably formed from a material which is resistant to the chemicals and environmental conditions within the washer chamber 20, such as a silicone material. DURO 60 is one particularly preferred material. With particular reference to FIGS. 3 and 4, the gasket 42 forms a seal between an outer-facing surface 46 of the inner panel 30 of the door frame and the inner glass pane 36 by the cooperative action of the connecting member 40 and fixing members, such as threadable screws 50 and 52, or horizontally extending threaded rods (not shown) which are welded to the connecting member and tightened adjacent an inner surface 53 of the inner panel 30 with locking nuts (not shown).

The gasket is partially compressed and remains soft over the operating temperatures and the life of the structure. The gasket compresses as the glass pane 36 expands at higher temperatures and expands as the glass contracts at lower temperatures, maintaining a humidity tight seal. Annular sealing members, such as TEFLON washers 54 and 56, between the screws 50 and 52 and the inner panel 30, provide a moisture-tight seal when the screws are tightened.

Figure 5:
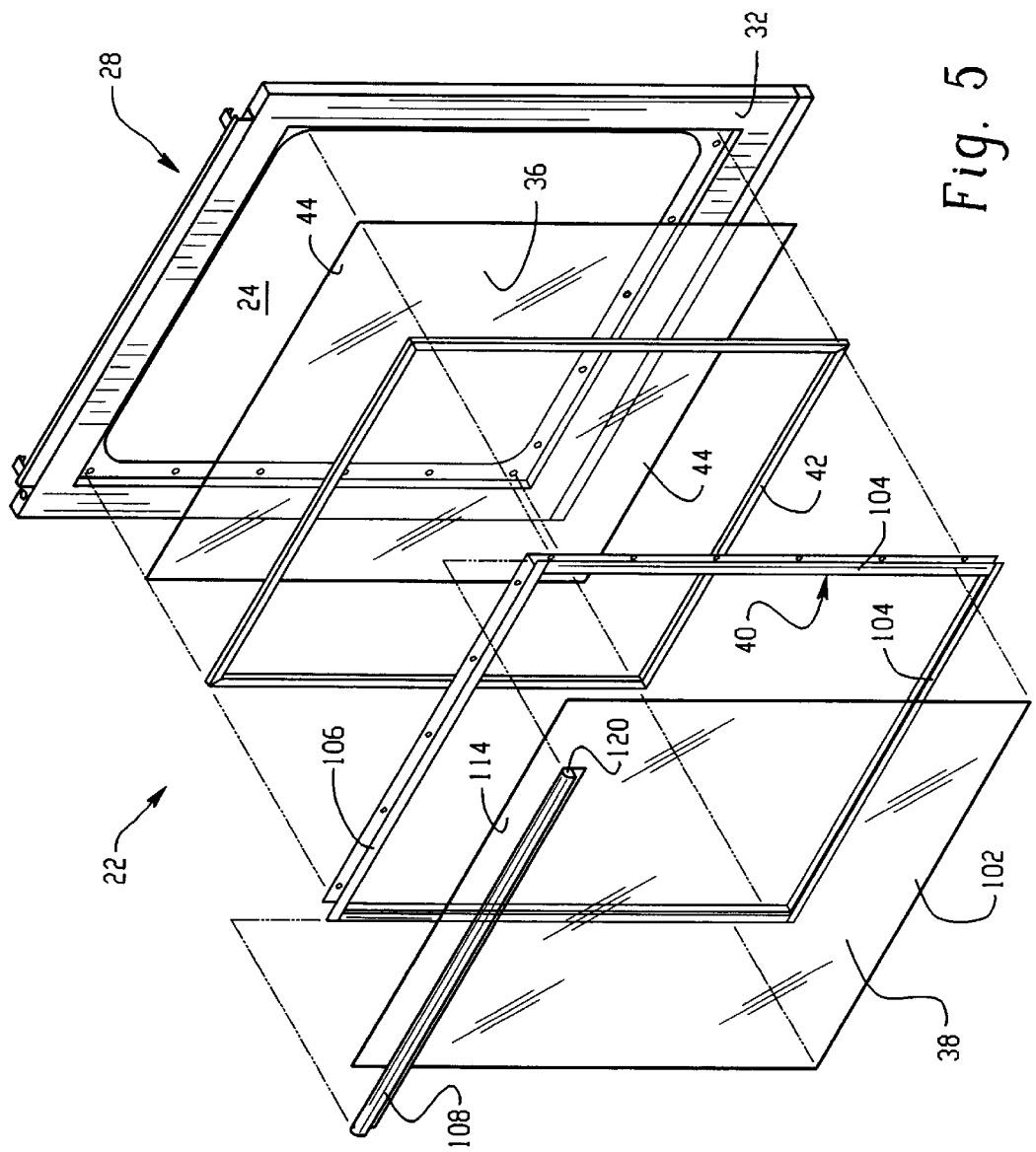
FIG. 5 is an exploded perspective view of a dismantlable door in accordance with the present invention.

The connecting member 40 serves two functions, namely to hold the inner glass pane 36 in a sealing relationship to the outer surface 46 of the inner panel and to support the outer glass pane 38 at a preselected distance from the inner glass pane. As best shown in FIG. 5, the connecting member defines a rectangular frame which runs adjacent four sides of the peripheral edge 44 of the inner glass pane. Specifically, the connecting member includes a central support 60, which lies perpendicular to the plane of the door frame, an inner or first flange 62 and an outer or second flange 64. The flanges extend perpendicularly from peripheral edges of the central support in a direction away from the inner glass pane 36. Together, the central support 60 and flanges 62 and 64 define a U-shaped groove 66. The groove has a width D which is sufficient to allow the outer flange 64 to lie adjacent to an outer surface 70 of the outer panel 32 when the connecting member 40 is moved to a sealing position in which the inner glass pane is held in position against the outer surface 46 of the inner panel.

The flanges 62, 64 are preferably of different lengths, the outer flange 64 being longer so that a portion of the flange overlaps a portion of the outer panel 32 in the sealing position. The inner flange 62 is shorter so that it is not arrested by the outer panel when the connecting member 40 is moved to the sealing position. Preferably, the inner flange is just short enough to enable it to pass without undue interference between the gasketed peripheral edge 44 of the inner glass pane 36 and the inner panel 32.

A third, or central flange 72 extends inward from the central support 60, in a direction opposite to that of the inner and outer flanges. When the connecting member 40 is in the sealing position, adjacent the outer surface 46 of the inner panel, the third flange 72 presses against an outer wall 74 of the U-shaped gasket 42 creating a seal between the connecting member and an outer surface 75 of the inner glass pane 36.

The tightening of the screws 50 and 52 also causes a seal to be formed between the outer surface 46 of the inner panel and an inner wall 76 of the U-shaped gasket 42, thus completing the seal between the frame 28, and the inner glass pane 36. Specifically, the threadable screw 50 passes through a suitably positioned aperture 78 in the inner panel 30 and a similar aperture 79 formed in the inner flange 62 at the upper end of the connecting member. The screw is screwed to a sufficient tightness to ensure the formation of the seal, without unduly deforming the U-shaped gasket 42. Similarly, threadable screw 52 passes through a suitably positioned aperture 80 in the inner panel 30 and a similar aperture 81 formed in the inner flange 62 of the lower end of the connecting member. However, even if the U-shaped gasket 42 degrades during use, it is readily replaced because the door is dismantlable. The inner and outer panes may be removed, as desired, and a new gasket 42 positioned on the inner glass pane 36.

Preferably, the connecting member extends adjacent the entire peripheral edge 44 of the inner glass pane 36 so that a complete seal is formed between the inner glass pane and the door frame and between the inner panel and the connecting member.

With continued reference to FIGS. 3 and 4, a support bracket 82 preferably connects the inner and outer panels 30,32 adjacent the connecting member 40 to maintain the desired spacing between the inner and outer panels. Preferably, a central opening 86 in a lower portion 84 of the support bracket 82 provides a drain hole for the escape of moisture. An additional aperture 88, at the lower end 34 of the door frame 28, allows the moisture to drain from the door. Inner and outer silicone joints 90 and 92 optionally seal around the door frame inner and outer panels 30,32 adjacent the support bracket 82.

In a first embodiment, best shown in FIG. 4, a U-shaped channel 100 is defined by a distal end of the outer flange 64. The U-shaped channel loosely receives at least a first peripheral edge 102 of the outer glass pane 38. Preferably, the channel 100 extends along one or more sides 104 of the connecting member 40, and more preferably along three sides 104 of the connecting member, as shown in FIG. 5. The channel is formed from a material which has sufficient strength to support the weight of the tempered glass outer pane, particularly during opening and closing of the door. The channel 100 preferably includes an aperture 105 in a lowest point to permit any condensate to flow down the glass, into the channel, and out the aperture.

In the first embodiment, as shown in FIGS. 3 and 5, at least one side 106 of the connecting member lacks the channel for ease of removal of the outer glass pane 38. The outer glass pane 38 is supported adjacent the side 106 of the connecting member by a removable support member 108. In cooperation, the U-shaped channel 100 and support member 108 hold the outer glass pane adjacent the outer flange 64. The support member defines a second channel 112 which receives a second peripheral edge 114 of the outer pane 38. The second peripheral edge may be an upper, horizontal edge of the outer glass pane, as shown in FIG. 5, or a vertical, side edge, as shown in FIG. 1. Preferably, the edge 114 is not the lower, horizontal edge of the outer glass pane, to reduce the risk of the outer glass pane falling from the connecting member 40 during operation. The second peripheral edge is also preferably opposite to the first peripheral edge 102.

The support member 108 is preferably gripped between the outer flange 64 of the connecting member and the outer surface 70 of the outer panel of the door frame. In this embodiment, the support member includes an arm 118 which is clamped between the outer surface 70 of the outer panel of the door and the outer flange 64, when the screws 50, 52 are tightened.

Optionally, the support member includes end caps 120, one on each end of the channel 112, to assist in maintaining the outer pane 38 in position.

Figure 2:
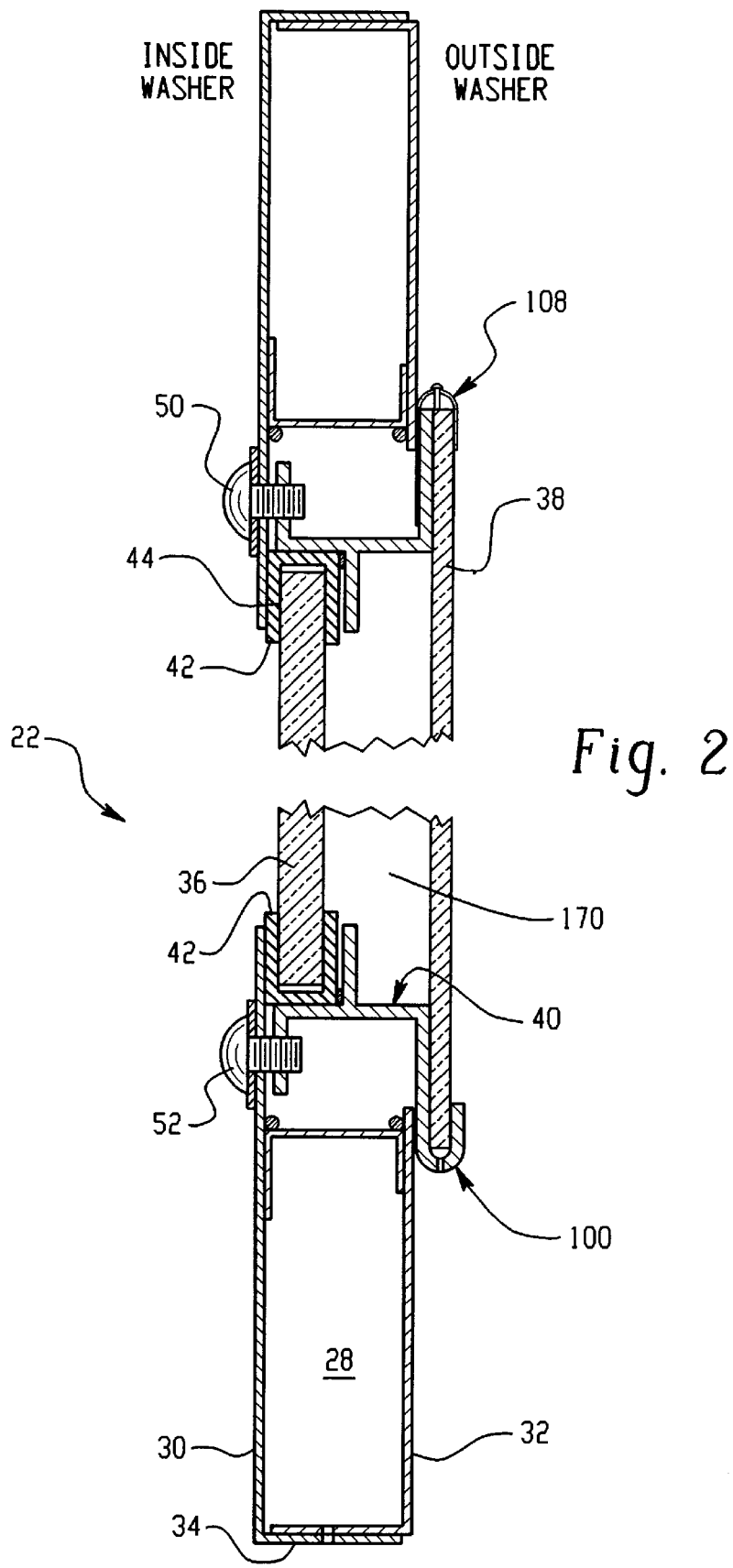
FIG. 2 is a side sectional view of the dismantlable door of FIG. 1.

To assemble the door, the gasket 42 is first fitted to the peripheral edge 44 of the inner glass pane 36. A small bead 122 of a semi-permanent sealant material, such as a silicone joint compound, is preferably applied to the connecting member in a right-angled corner defined between the central support 60 and the third flange 72 to assist in providing a seal between the outer surface 74 of the U-shaped gasket 42 and the connecting member 40. Additionally, a sealing member, such as a silicone gasket 124, is preferably inserted between the outer panel 32 and a lower end 125 of the outer, second flange 64. The inner glass pane 36 is then positioned adjacent the inner door panel 30 and the connecting member 40 is held against the U-shaped gasket so that the inner flange 62 of the connecting member lies adjacent the outer surface 46 of the inner panel, as shown in FIG. 2. The screws 50 and 52 are then inserted through their respective apertures 78, 79, 80, 81 in the inner panel 30 and inner flange 62 and tightened until the desired seal is formed. Additional screws may be used as necessary to form an even seal around the peripheral edge of the inner glass pane 36. The outer pane 38 is then inserted into the connecting member 40 in the direction of arrow A. The support member 108 is inserted between the outer door panel 32 and the outer flange 64 once the outer glass pane is received in the U-shaped channel 100. Some adjustment of the screw 50 may be necessary to insert the removable support member 108 and apply a final tightening after the removable support has been inserted.

Alternative assembly methods are also contemplated. For example, the outer glass pane 38 may be inserted into the connecting member 40 before inserting the screws 50, 52.

The outer glass pane 38 may be removed for cleaning of the panes or for replacement of the outer pane, without fully removing the connecting member 40. To remove the outer pane, the removable support member 108 is removed or withdrawn and the outer pane slid from the connecting member in a direction opposite to arrow A. Some slight adjustment to screw 50 may be necessary to allow the removal of the removable support member 108. Once the panes have been cleaned, the outer pane can be reinserted in the connecting member. To remove both of the glass panes 36 and 38, the screws are simply fully unscrewed.

Alternatively, a fixing member, such as a support screw or bolt 126, is threaded through an aperture 128 in the removable support member 108 so that it enters the channel 112. The support screw is tightened until it engages the upper end 114 of the outer pane 38 to hold the pane in position. To remove the outer pane for cleaning, the support screw is loosened until the pane can be removed from the support member. This allows the outer glass pane to removed without the removal of the support member 108.

Figure 6:
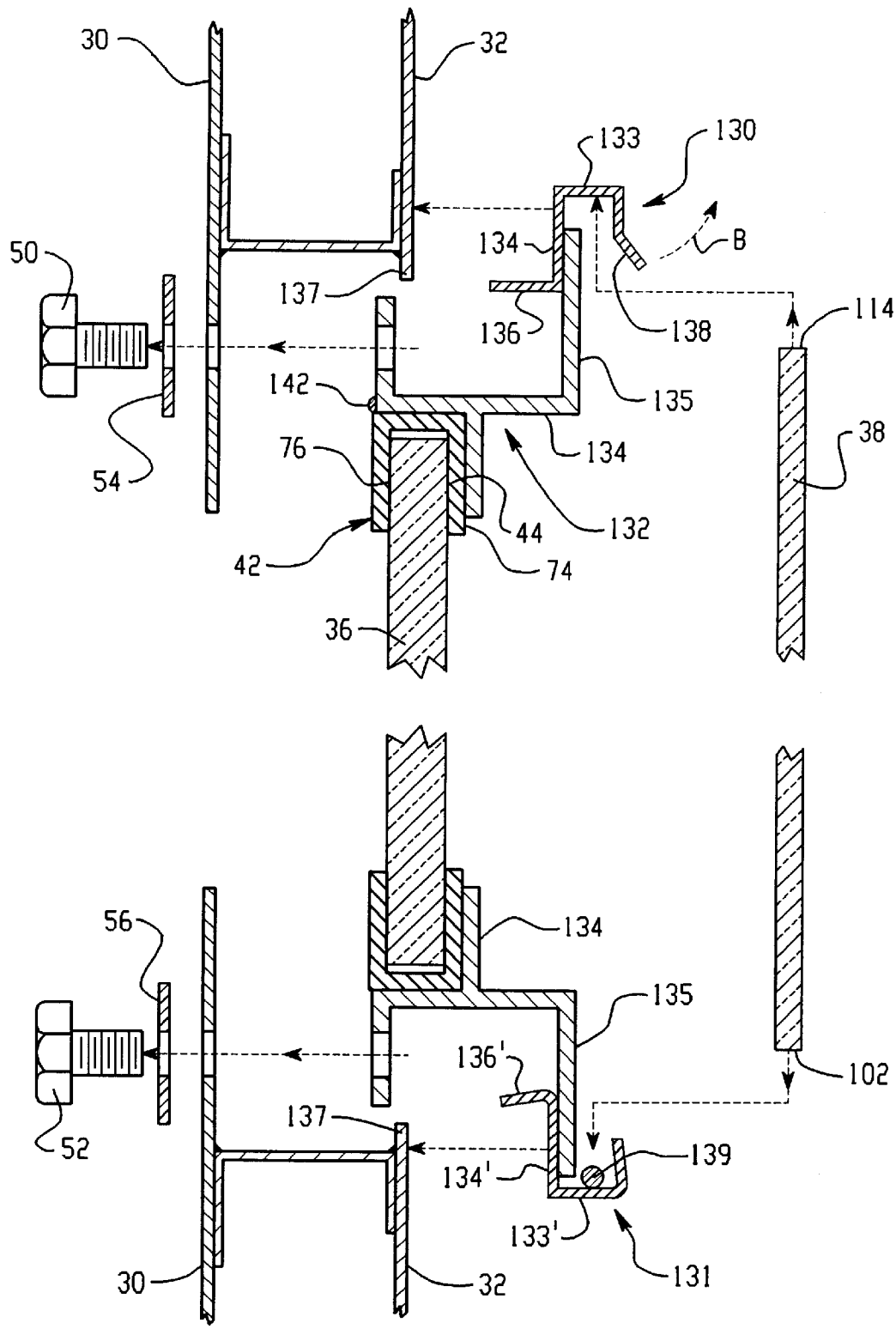
FIG. 6 is an exploded side sectional view of the dismantlable door of FIG. 1 in accordance with a second embodiment of the present invention.

In a second embodiment, shown in FIG. 6, two removable support members 130 and 131, rather than a single removable support member, are used at opposite ends of a connecting member 132. As shown in FIG. 6, the two support members are upper and lower support members, although the use of support members adjacent vertical sides of the outer pane 38 is also contemplated. In other respects, the connecting member 132 is the same as the connecting member 40, shown in FIGS. 3 and 4. Other parts of the door are similar to those of FIGS. 3 and 4, and are numbered accordingly.

In one version of this embodiment, the upper and lower support members 130,131 are configured in a similar manner to the support member 108 of FIG. 3. In this version, the outer pane 38 is removed by loosening the screw 50 and releasing the upper support member 130. Or, a support screw (not shown), similar to the support screw 126 of FIG. 3, is loosened to allow removal of the outer pane without removal or upward displacement of the support member.

In a second version of this embodiment, shown in FIG. 6, at least the upper support member 130 is formed from a resiliently flexible material. Both of the support members include a U-shaped channel 133,133', respectively, which receives the respective end 114,102 of the outer pane therein. As for the channel 100 of FIG. 5, the channel 133' of the lower support member optionally runs adjacent three of the peripheral sides of the outer glass pane. An inner arm 134,134' of each of the U-shaped channels is received between an outer flange 135 of the connecting member and the outer panel 32. A flange 136,136' extends inward from the distal end of each of the inner arms 134,134' and lies adjacent a central perimeter 137 of the outer panel 32 when the door is assembled. The flanges aid in positioning the support members during assembly of the door. The U-shaped channel 133 of at least the upper support member 130 includes an outer arm 138 which may be flexed outward, away from the outer pane 38.

Optionally a cushioning gasket 139 is positioned along the length of the channel 133' defined in the lower support member 131. A silicone joint 142 is applied to an inward facing corner defined between the connecting member and the U-shaped gasket, taking care not to extend the joint material beyond the inner wall 76 of the U-shaped gasket.

The door is assembled in a similar manner to that of the first embodiment, except in the following respects. The upper and lower support members 130 and 131 are held with their inner arms 134 and 134' between the outer panel 32 of the door and the flange 135 of the connecting member 132 while the connecting member, together with the inner glass pane 36, is joined to the inner panel 30 by the screws 50 and 52. The outer pane 38 is then slotted by its lower end 102 into the lower support member where it rests on the gasket 139. The outer arm 138 of the upper support member 130 is flexed outward and the upper end 114 of the outer pane pivoted until it is received against the outer flange 135 of the connecting member. The outer arm of the upper support member is then allowed to flex back into position so that the upper end of the outer pane is firmly gripped between the outer arm 138 of the upper support member and the flange 135 of the connecting member.

To remove the outer pane for cleaning, the outer arm 138 of the upper removable support member is flexed outwardly, in the direction of arrow B, and the upper end 114 of the outer glass pane is pivoted outward, away from the connecting member. This can be done by pulling the outer arm 138 outward or by pulling the vertical sides of the outer pane outward, adjacent the upper end 114, pushing the outer arm outward in the process. The outer glass pane 38 is then lifted upwardly to remove the pane from the lower support member 131.

Figure 7:
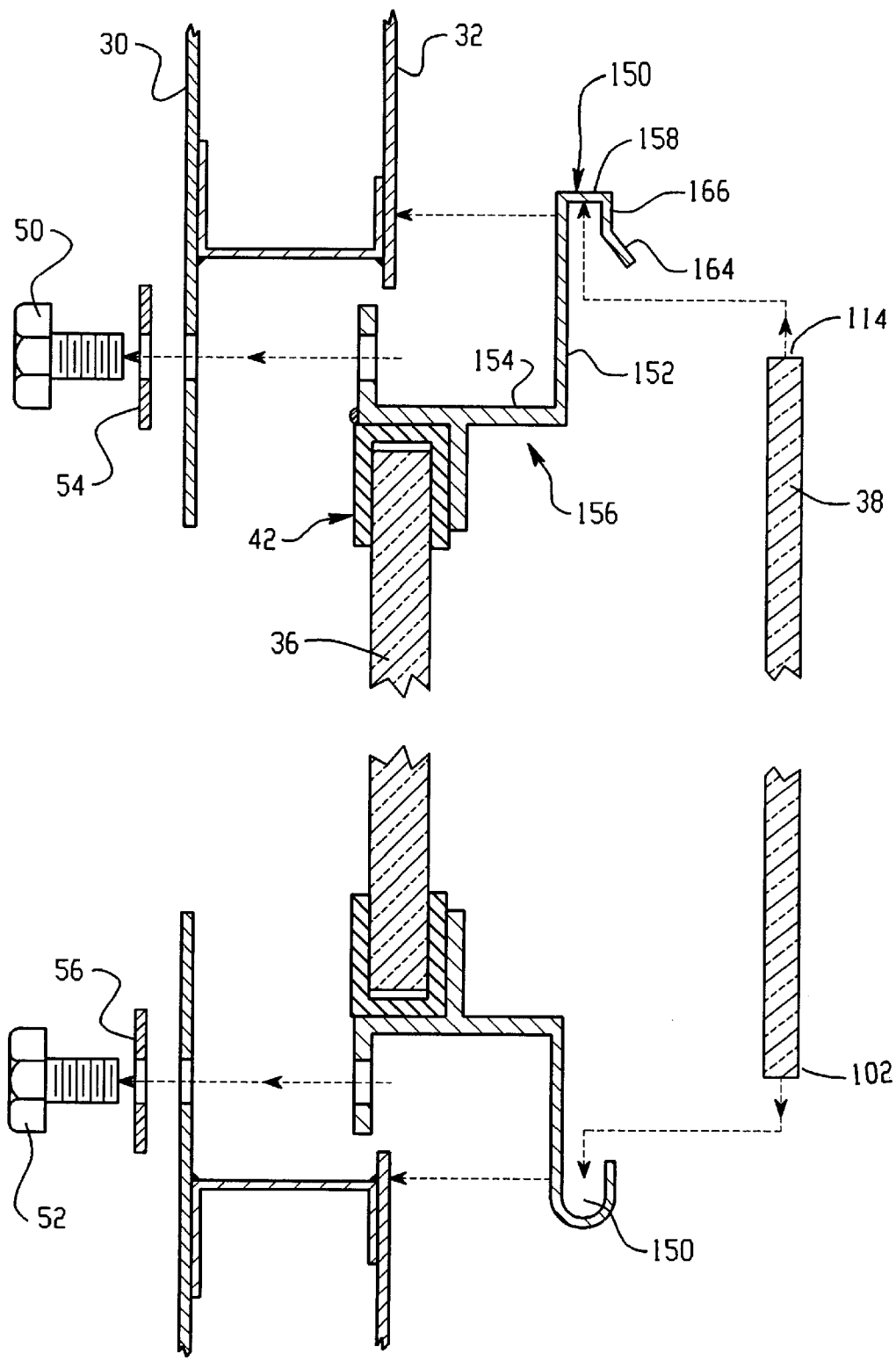
FIG. 7 is an exploded side sectional view of the dismantlable door of FIG. 1 in accordance with a third embodiment of the present invention.

In a third embodiment, shown in FIG. 7, a support member 150 forms an integral part of an outer flange 152 on all four sides of a connecting member 156. The support member may be formed from the same material as the outer flange, or formed from another material which is bonded to the outer flange. The connecting member is otherwise the same as for the connecting member 40 of FIGS. 3 and 4. The support member includes a U-shaped channel 158 for receiving the upper end 114 of the outer pane 38. An outer arm 164 of at least an upper end 166 of the U-shaped channel flexes outwardly, as for the arm 138 of the embodiment of FIG. 6, to receive the upper end of the outer pane. Once the outer glass pane is fully inserted, the support member flexes back and grips the peripheral upper end 114 in the channel 160.

Figure 8:
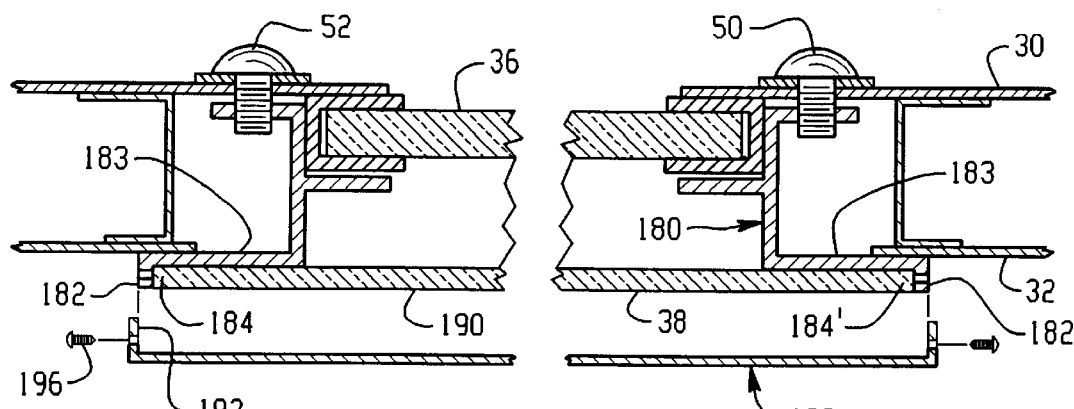
FIG. 8 is a partially exploded side sectional view of the dismantlable door of FIG. 1 in accordance with a fourth embodiment of the present invention.
Figure 9:
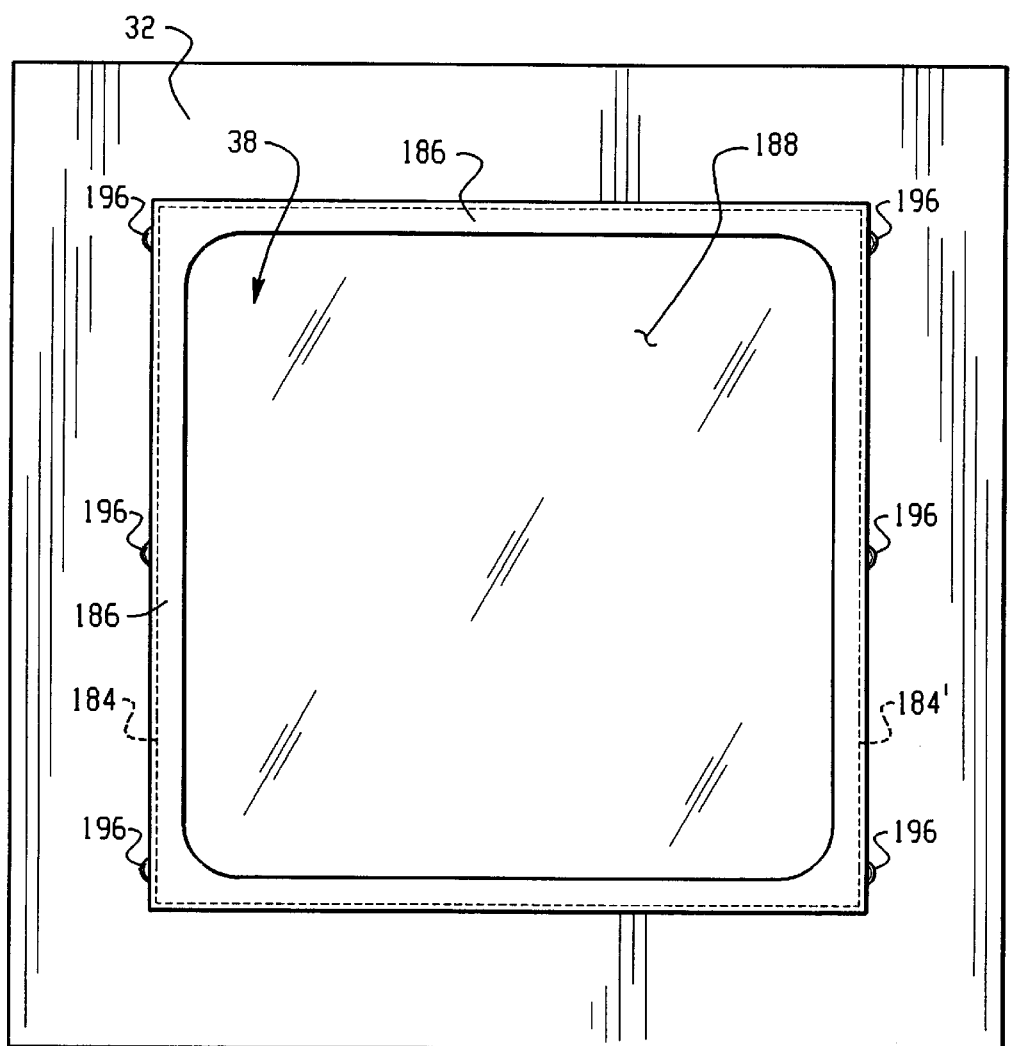
FIG. 9 is a front elevational view of the dismantlable door of FIG. 8.

With reference to FIGS. 8 and 9, a fourth embodiment is shown. A connecting member 180 is similar to the connecting member 40, except in that instead of a U-shaped channel 100, a peripheral support 182 extends orthogonally from an outer flange 183 on at least two opposing sides of the connecting member, adjacent two peripheral edges 184,184' of the outer glass pane 38. As shown in FIG. 9, these edges are vertical edges of the outer pane, although it is also contemplated that the peripheral support 182 runs around all four edges of the outer glass pane or on upper and lower edges only. An outer frame 186 having a central, generally rectangular central opening 188, through which the outer glass pane is exposed, is positioned adjacent an outer surface 190 of the outer glass pane. A peripheral flange 192 of the outer frame overlaps the peripheral support 182. It is preferable that at least a lower edge 194 of the outer glass pane is supported by either the outer frame flange 192 or the connecting member peripheral support 182 to prevent the outer pane from falling from the door. Fixing members, such as screws 196, are inserted through openings in the peripheral flange 192 and corresponding openings in the peripheral support until they tighten on the peripheral edges 184, 184' of the outer glass pane.

With reference to FIG. 10 a fifth embodiment having a connecting member 200 substantially as the connecting member 40 of the first embodiment is shown, except in that instead of instead of a U-shaped channel 100, at least two resiliently flexible supports 202,202' extend away from the connecting member from at least two opposing peripheral edges 204,206 of an outer flange 208 of the connecting member. An acute angle is defined between each of the supports and the flange. The outer pane 38 is held by the supports 202,202'. Preferably the supports 202,202' support at least upper and lower peripheral edges 114 and 102, respectively, of the outer glass pane. The outer pane can be removed from or inserted into the support by flexing one or more of the supports outwards, away from the outer pane of glass.

With reference to FIG. 11, a sixth embodiment similar to that of the embodiment of FIGS. 2 and 3 is shown. A removable support member 210, for supporting the upper end 114 of the outer pane 38 is similar to the removable support member 108. However, the support member 210 is held between an inner surface 212 of the outer glass pane 38 and the outer surface 70 of the door frame outer panel 32, rather than between an outer flange 214 of a connecting member 216 and the outer surface 70. As for the embodiment of FIGS. 2, and 3, a U-shaped channel 100, depending from the adjacent portion of the outer flange 64 supports the lower peripheral edge 102 of the outer glass pane. The support member 210 is removable in the same manner as for the removable support member 108 or may be removable without loosening of the screw 50. The outer glass pane is removed from the connecting member 216 in the direction of arrow B.

With reference to FIG. 12, a seventh embodiment uses a connecting member 220 similar to the connecting member 40 of the first embodiment, except in that there is no U-shaped channel 100. The connecting member 220 has an outer flange 221 which contacts the inner surface 212 of the outer glass pane 38 adjacent at least two and preferably four peripheral edges of the outer pane. To support the outer glass pane 38, a pair of L-shaped support members 222 and 224 are connected with first, longer legs 226 and 228 of each L being removably connected to ends 33 and 34 of the door frame 28 by fixing members, such as screws 230 and 232 such that the second, shorter legs 233,234 of each L overlap an outer surface 235 of the outer glass pane adjacent peripheral edges 236 and 238. The peripheral edges 236,238 are preferably top and bottom edges of the outer glass pane 38. In this embodiment, the outer glass pane extends the full length of the door frame 28.

With reference to FIG. 13, an eighth embodiment is similar to the seventh embodiment of FIG. 12, except in that a single removable L-shaped support member 240 supports an upper peripheral edge 114 of the outer glass pane, while a U-shaped channel 242 supports the lower peripheral edge 102. The U-shaped channel 242 may be adhered to the outer surface 70 of the outer panel 32 of the door frame, with adhesive or suitable fixing members as shown in FIG. 13, or may be attached to a lower portion of an outer flange 243 of a connecting member 244, as for the U-shaped channel 100 of FIGS. 2 and 4. A fixing member, such as a screw 246, releasably connects the L-shaped flange to the upper end 33 of the door frame 28.

Figure 14:
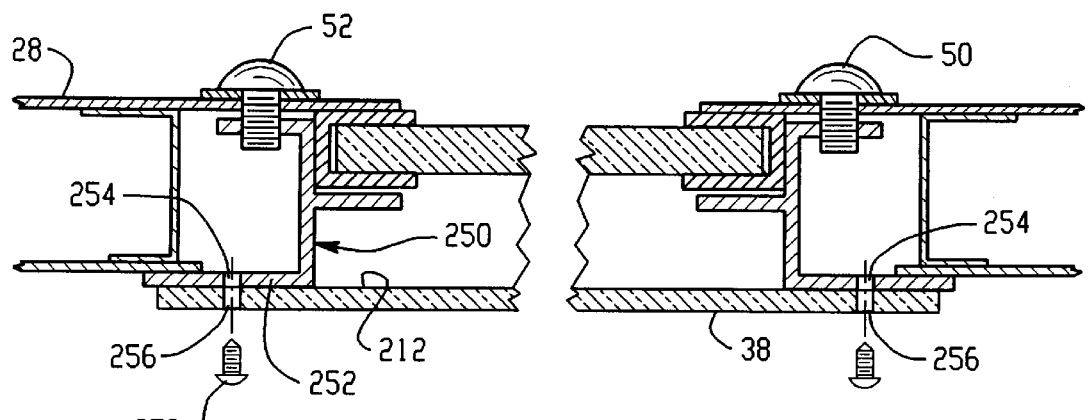
FIG. 14 is a side sectional view of the dismantlable door of FIG. 1 in accordance with a ninth embodiment of the present invention; and, FIG. 15 is a front elevational view of the dismantlable door of FIG. 14.
Figure 15:
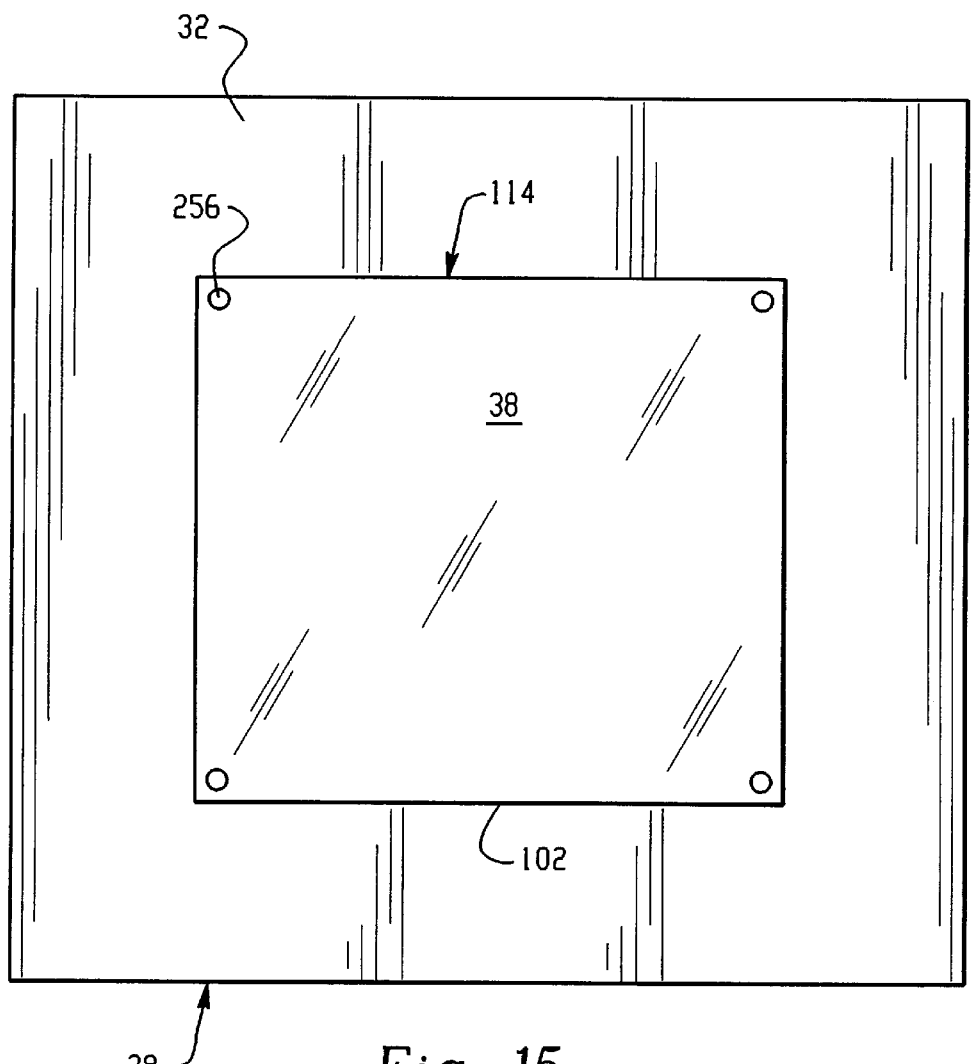

With reference to FIGS. 14 and 15, a ninth embodiment is shown. A connecting member 250, similar to connecting members 220 and 244, includes an outer flange 252 which contacts the inner surface 212 of the outer glass pane 38, as for the embodiment of FIG. 13. In this embodiment the flange includes at least four apertures 254, adjacent four corners of the outer glass pane. Corresponding apertures 256 are drilled through the outer glass pane. Fixing members, such as screws 258, pass through the pane apertures 256 and the flange apertures 254 to releasably connect the outer glass pane 38 to the connecting member 250.

The configuration of the connecting members 40, 132, 156, 180, 200, 216, 220, 244 and 250 and inner and outer glass panes of each of the embodiments allows each pane to react independently to temperature changes. The outer pane 38 is not sealed to the connecting member. This allows air to enter between the two panes, equilibrating the air pressure in an air space 170 defined between the two panes (see FIG. 2). The ventilated air space 170 allows the outer pane 38 to remain relatively cool to the touch during a cleaning cycle without fogging occurring between the glass panes.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A washer including a washing chamber for receiving items to be washed at elevated temperatures using chemical detergents and a dismantlable door for permitting selective access for loading items into and unloading items from the washing chamber, the door comprising:
    a support frame;
    an inner transparent pane;
    an outer transparent pane; and,
    a connecting member, the connecting member configured for selectively maintaining the inner transparent pane and the frame in a sealing relation and for selectively receiving the outer transparent pane in an unsealed relation to the frame.

2. The washer of claim 1, further including a sealing member disposed between the support frame and the inner transparent pane.

3. The washer of claim 2, wherein the sealing member includes a U-shaped gasket which extends around an outer edge of the inner transparent pane.

4. The washer of claim 3, wherein the U-shaped gasket selectively seals the inner transparent pane to the connecting member.

5. The washer of claim 1, wherein the inner transparent pane and the outer transparent pane define an airspace therebetween.

6. The washer of claim 1, wherein the support frame includes:
    an inner panel; and,
    an outer panel; and the connecting member includes:
        a central support;
        an inner flange which extends from the central support and is releasably attached to the inner panel;
        a central flange which extends from the central support adjacent an outer surface of the inner transparent pane; and,
        an outer flange which engages the outer panel of the support frame.

7. The washer of claim 6, wherein the outer flange engages an outer surface of the outer panel.

8. The washer of claim 6 further including:
    fixing members for connecting the inner flange to the inner panel; and,
    a gasket around an outer edge of the inner transparent pane such that the gasket is compressed by the central flange as the fixing members draw the inner flange to the inner panel.

9. The washer of claim 1, wherein the connecting member defines a channel which selectively receives at least a first edge of the outer transparent pane.

10. The washer of claim 9, further including a support member which selectively receives a second edge of the outer transparent pane when the outer transparent pane is received by the channel.

11. The washer of claim 10, wherein the support member includes an arm which is selectively gripped between the support frame and a flange of the connecting member.

12. The washer of claim 10, wherein the support member is resiliently flexible, whereby the support member flexes to allow the outer transparent pane to be received by the channel.

13. The washer of claim 10, wherein the support member includes an L-shaped flange having a first leg which is attached to an upper end of the door frame and a second leg which extends from the first leg adjacent an exterior surface of the outer glass pane.

14. The washer of claim 1, further including:
    a first support member which defines a first channel for receiving a first side of the outer transparent pane and an inner arm which is selectively trapped between the connecting member and the support frame; and,
    a second support member for receiving a second, opposite side of the outer transparent pane.

15. The washer of claim 14, wherein the second support member is connected with a front face of the door frame and defines a second channel for receiving the second, opposite side of the outer transparent pane.

16. The washer of claim 14 wherein the second support member defines a second channel and includes an inner arm which is selectively trapped between the connecting member and the support frame.

17. The washer of claim 16, wherein at least one of the first and second support member channels includes a resiliently flexible outer arm which flexes outward for insertion and removal of the outer transparent pane.

18. The washer of claim 14, wherein the second support member includes an L-shaped flange, a first leg of the L-shaped flange being removably connected with a lower edge of the door frame and a second leg of the L-shaped flange extending adjacent a periphery of an outer surface of the outer glass pane.

19. A connecting assembly for selectively maintaining an inner transparent pane in sealing relation with a washer door frame and for selectively receiving an outer transparent pane, the connecting assembly comprising:
    a first peripheral flange which is configured for attachment to an inner door frame panel;
    a second peripheral flange for selectively engaging an outer face of an outer door frame panel, the second peripheral flange defining a channel at least partially along at least a lower edge for receiving at least a lower edge of the outer transparent pane;

a third peripheral flange for pressing a peripheral edge of the inner transparent pane between the third peripheral flange and an outer face of the inner door panel; and, the second and third flanges configured for positioning the inner and outer transparent panes in a spaced relationship such that an airspace is defined therebetween.

20. The connecting assembly of claim 19, further including a gasket around a peripheral edge of the inner transparent pane compressed between the inner transparent pane and at least one of the third flange and the inner panel outer face.

21. The connecting assembly of claim 19 further including threaded members for attaching the first flange to the inner door frame panel, the threaded members drawing the third flange and the inner panel together to compress the gasket.

22. The connecting assembly of claim 19, further including a resilient support for receiving a second edge of the outer transparent pane.

23. A washer including a washing chamber for receiving items to be washed at elevated temperatures and an opening in the chamber, a window assembly covering the opening for providing a view into the chamber through the opening, the assembly comprising:

a support frame;

an inner glass pane;

an outer glass pane; and, a connecting member, the connecting member configured for selectively maintaining the inner glass pane and the frame in a sealing relation and for selectively receiving the outer glass pane in an unsealed relation to the frame.

24. The washer of claim 1 wherein the channel includes a resiliently flexible outer arm which flexes outward for insertion and removal of the outer transparent pane.

* * * * *